US010100337B2

(12) United States Patent
Bell et al.

(10) Patent No.: US 10,100,337 B2
(45) Date of Patent: *Oct. 16, 2018

(54) PROCESS FOR FERMENTING CO-CONTAINING GASEOUS SUBSTRATES

(71) Applicant: INEOS BIO SA, Rolle (CH)

(72) Inventors: Peter Simpson Bell, Dunblane (GB); Song Liu, Fayetteville, AR (US)

(*) Notice: Subject to any disclaimer, the term of this patent is extended or adjusted under 35 U.S.C. 154(b) by 81 days.

This patent is subject to a terminal disclaimer.

(21) Appl. No.: 14/176,094

(22) Filed: Feb. 9, 2014

(65) Prior Publication Data

US 2014/0308723 A1    Oct. 16, 2014

Related U.S. Application Data

(60) Provisional application No. 61/764,840, filed on Feb. 14, 2013.

(51) Int. Cl.
*C12P 7/06* (2006.01)
*C12P 3/00* (2006.01)

(52) U.S. Cl.
CPC ...... *C12P 7/06* (2013.01); *C12P 3/00* (2013.01); *C12P 7/065* (2013.01); *Y02E 50/17* (2013.01)

(58) Field of Classification Search
None
See application file for complete search history.

(56) References Cited

U.S. PATENT DOCUMENTS

2010/0227377 A1* 9/2010 Adams .............. C12N 1/20
435/252.7

FOREIGN PATENT DOCUMENTS

WO      0208438        1/2002
WO    2009151342      12/2009

OTHER PUBLICATIONS

Michael Kopke et al: 'Fermentative production of ethanol from carbon monoxide', Current Opinion in Biotechnology, vol. 22, No. 3, Jun. 1, 2011 (Jun. 1, 2011), pp. 320-325, XP055104855, ISSN: 0958-1669, DOI: 10.1016/j.copbio.2011.01.005 p. 321, right-hand column, last paragraph-p. 323, left-hand column, paragraph 1; table 2.

Munasinghe P C et al: "Biomass-derived syngas fermentation into biofuels: Opportunities and challenges", Bioresource Technology, Elsevier BV, GB, vol. 101, No. 13, Jul. 1, 2010 (Jul. 1, 2010), pp. 5013-5022, XP026986241, ISSN: 0960-8524 [retrieved on Mar. 27, 2010] p. 5016, right-hand column, paragraph 1-p. 5018, left-hand column, paragraph 3; table 3.

S.S. Riggs et al: "Measuring Carbon Monoxide Gas-Liquid Mass Transfer in a Stirred Tank Reactor for Syngas Fermentation", Biotechnology Progress, vol. 22, No. 3, Jun. 2, 2006 (Jun. 2, 2006), pp. 903-906, XP055095229, ISSN: 8756-7938, DOI: 10.1021/bp050352f abstract p. 903, right-hand column, last paragraph-p. 906, left-hand column, paragraph 2.

Cotter J L et al: "Influence of process parameters on growth of Clostridium Ijungdahlii and Clostridium autoethanogenum on synthesis gas", Enzyme and Microbial Technology, Stoneham, MA, US, vol. 44, No. 5, May 6, 2009 (May 6, 2009), pp. 281-288, XP026004172, ISSN: 0141-0229, DOI: 10.1016/J.ENZMICTEC. 2008.11.002 [retrieved on Nov. 17, 2008] abstract p. 283, left-hand column, paragraph 1-p. 288, left-hand column, last paragraph.

Maedeh Mohammadi et al: "Kinetic Studies on Fermentative Production of Biofuel from Synthesis Gas Using Clostridium Ijungdahlii", The Scientific World Journal, vol . 27, No. 2, Jan. 1, 2014 (Jan. 1, 2014), pp. 185-188, XP055122952, ISSN: 2356-6140, DOI: 10.1016/j.biortech.2005.05.014 abstract, p. 4, right-hand column, paragraph 2-p. 6, right-hand column, paragraph 2.

International Searching Authority, Annex to Form PCT ISA/206 Communication Relating to the Results of the Partial International Search issued in PCT/US2014/015892, dated Jun. 23, 2014, 3 pages.

* cited by examiner

*Primary Examiner* — Jennifer M. H. Tichy
(74) *Attorney, Agent, or Firm* — James P. Krueger

(57) ABSTRACT

A process provides high ethanol productivity levels during fermentation of a CO-containing substrate. The process controls CO-substrate feed rates and cell density to avoid culture upset and CO inhibition. The process includes fermenting a CO-containing gaseous substrate to obtain a target cell density and a target CO feed rate, and then periodically reducing and increasing the CO feed rate.

5 Claims, 7 Drawing Sheets

PROCESS FOR FERMENTING CO-CONTAINING GASEOUS SUBSTRATES

This application claims benefit of U.S. Provisional Application Ser. No. 61/764,840 filed on Feb. 14, 2013, all of which is incorporated in its entirety herein by reference.

A process is provided for fermenting CO-containing gaseous substrates. More specifically, the process includes fermenting the CO-containing gaseous substrate to obtain a target cell density and a target CO feed rate, and then periodically reducing and increasing the CO feed rate. The process is effective for maintaining a dissolved CO concentration in the fermentation of about 0.25 mM or less.

BACKGROUND

Acetogenic microorganisms can produce ethanol from carbon monoxide (CO) through fermentation of gaseous substrates. Fermentations using anaerobic microorganisms from the genus *Clostridium* produce ethanol and other useful products. For example, U.S. Pat. No. 5,173,429 describes *Clostridium ljungdahlii* ATCC No. 49587, an anaerobic microorganism that produces ethanol and acetate from synthesis gas. U.S. Pat. No. 5,807,722 describes a process and apparatus for converting waste gases into organic acids and alcohols using *Clostridium ljungdahlii* ATCC No. 55380. U.S. Pat. No. 6,136,577 describes a process and apparatus for converting waste gases into ethanol using *Clostridium ljungdahlii* ATCC No. 55988 and 55989.

Processes for producing ethanol from carbon monoxide involve culturing the acetogenic bacteria on increasing amounts of CO over time. High or low levels of CO in the fermentation may result in lower productivity. As CO feed rates to the fermentor increase, dissolved CO concentrations in the fermentation medium may increase. The increase in dissolved CO concentration in the fermentation medium may result in CO-inhibition and decreased levels of productivity.

SUMMARY

A process provides high ethanol productivity levels during fermentation of a CO-containing substrate. The process controls CO-substrate feed rates and cell density to avoid culture upset and CO inhibition.

A process for fermenting a CO-containing substrate includes providing the CO-containing substrate to a fermentor to obtain a target CO feed rate and maintaining a CO feed rate within about seven standard deviations of the target CO feed rate. The CO feed rate is effective for maintaining a dissolved CO concentration in the fermentation of about 0.25 mM or less and an STY of 10 g total alcohol/(L·day) or more. In one aspect, the process includes cycling the CO feed rate between a target CO feed rate and about seven standard deviations from the target CO feed rate. In another aspect, the CO feed rate is maintained within about four to about seven standard deviations of the target CO feed rate for at least about 1% to about 20% of a total fermentation time after achieving the target CO feed rate. In another aspect, the CO feed rate is maintained within about three to about five standard deviations of the target CO feed rate for at least about 1% to about 10% of a total fermentation time after achieving the target CO feed rate. In another aspect, the CO feed rate is maintained within about one to about three standard deviations of the target CO feed rate for at least about 1% to about 10% of a total fermentation time after achieving the target CO feed rate.

A process for fermenting a CO-containing substrate includes providing the CO-containing substrate to a fermentor and fermenting the CO-containing substrate to obtain a target cell density and a target CO feed rate. The process further includes reducing the target CO feed rate by about 35% or less to provide a reduced CO feed rate, maintaining the reduced CO feed rate for about 20 minutes or less, and returning the reduced CO feed rate to the target CO feed rate. The process is effective for providing an STY of 10 g total alcohol/(L·day) or more.

A process for fermenting a CO-containing substrate includes providing the CO-containing substrate to a fermentor, fermenting the CO-containing substrate to obtain a target cell density and a target CO feed rate; and maintaining a dissolved CO concentration in the fermentation of about 0.25 mM or less. In this aspect, the process is effective for providing an STY of 10 g ethanol/(L·day) or more. In another aspect, the dissolved CO concentration is maintained by: a) reducing the target CO feed rate to the fermentation by about 25% to about 35% of the target CO feed rate to provide a first reduced CO feed rate, and maintaining the first reduced CO feed rate for about 1 to about 10 minutes; b) increasing the first reduced CO feed rate to the fermentation to a provide a second reduced CO feed rate that is reduced by about 15 to about 25% of the target CO feed rate, and maintaining the second reduced feed rate for about 1 to about 5 minutes; c) increasing the second reduced CO feed rate to the fermentation to a provide a third reduced CO feed rate that is reduced by about 5% to about 15% of the target CO feed rate, and maintaining the third reduced feed rate for about 1 to about 5 minutes; and d) increasing the third reduced CO feed rate to the target feed rate or more. In one aspect, steps a) through d) are repeated at least about once per hour.

In another aspect, a process to avoid CO inhibition during fermentation of a CO-containing substrate includes providing the CO-containing substrate to a fermentor and contacting the CO-containing substrate with a fermentation medium and fermenting the CO-containing substrate. The process includes determining a dissolved CO concentration in the fermentation medium and maintaining a dissolved CO concentration in the fermentation of about 0.25 mM or less. The process is effective for providing an STY of 10 g ethanol/(L·day) or more.

In another aspect, a process for fermenting a CO-containing substrate includes providing the CO-containing substrate to a fermentor and fermenting the CO-containing substrate to obtain a target cell density and a target CO feed rate. The process includes maintaining a $H_2$ conversion of at least about 25% or more. The process is effective for providing an STY of 10 g ethanol/(L·day) or more.

In another aspect, a process for fermenting a CO-containing substrate includes providing the CO-containing substrate to a fermentor and fermenting the CO-containing substrate to obtain a target $H_2$ conversion and target CO uptake. The process includes monitoring the $H_2$ conversion and CO uptake and maintaining an $H_2$ conversion of about 25% to about 95% and a CO uptake of about 0.001 to about 10 mmole/minute/gram of dry cells.

BRIEF DESCRIPTION OF FIGURES

The above and other aspects, features and advantages of several aspects of the process will be more apparent from the following figures.

DETAILED DESCRIPTION

Figure 1A:
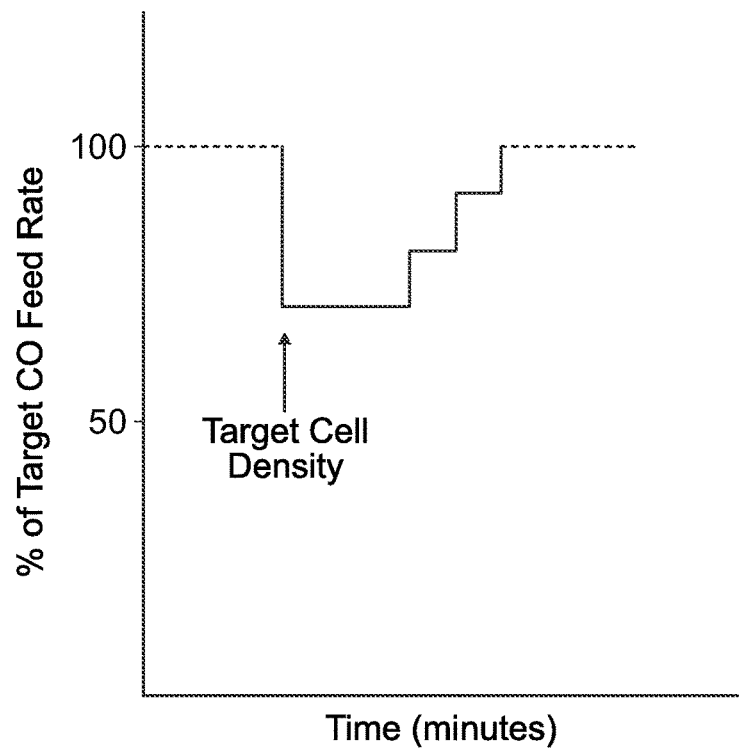
FIGS. 1A and 1B show repetitive patterns of cycling of CO to a fermentation.

The following description is not to be taken in a limiting sense, but is made merely for the purpose of describing the general principles of exemplary embodiments. The scope of the invention should be determined with reference to the claims.

Syngas fermentations conducted in bioreactors with medium and acetogenic bacteria as described herein are effective for providing conversions of CO in syngas into alcohols and other products. Control of CO concentrations in the fermentation through control of CO feed rates and cell density in the fermentation medium is effective for providing high productivity levels. In this aspect, productivity may be expressed as STY (space time yield expressed as g total alcohol/(L·day). In this aspect, the process is effective for providing a STY (space time yield) of at least about 10 g total alcohol/(L·day). Possible STY values include about 10 g total alcohol/(L·day) to about 200 g total alcohol/(L·day), in another aspect, about 10 g total alcohol/(L·day) to about 160 g total alcohol/(L·day), in another aspect, about 10 g total alcohol/(L·day) to about 120 g total alcohol/(L·day), in another aspect, about 10 g total alcohol/(L·day) to about 80 g total alcohol/(L·day), in another aspect, about 20 g total alcohol/(L·day) to about 140 g total alcohol/(L·day), in another aspect, about 20 g total alcohol/(L·day) to about 100 g total alcohol/(L·day), in another aspect, about 40 g total alcohol/(L·day) to about 140 g total alcohol/(L·day), and in another aspect, about 40 g total alcohol/(L·day) to about 100 g total alcohol/(L·day).

Definitions

Unless otherwise defined, the following terms as used throughout this specification for the present disclosure are defined as follows and can include either the singular or plural forms of definitions below defined:

The term "about" modifying any amount refers to the variation in that amount encountered in real world conditions, e.g., in the lab, pilot plant, or production facility. For example, an amount of an ingredient or measurement employed in a mixture or quantity when modified by "about" includes the variation and degree of care typically employed in measuring in an experimental condition in production plant or lab. For example, the amount of a component of a product when modified by "about" includes the variation between batches in a multiple experiments in the plant or lab and the variation inherent in the analytical method. Whether or not modified by "about," the amounts include equivalents to those amounts. Any quantity stated herein and modified by "about" can also be employed in the present disclosure as the amount not modified by "about".

The term "gaseous substrate" is used in a non-limiting sense to include substrates containing or derived from one or more gases.

The term "syngas" or "synthesis gas" means synthesis gas which is the name given to a gas mixture that contains varying amounts of carbon monoxide and hydrogen. Examples of production methods include steam reforming of natural gas or hydrocarbons to produce hydrogen, the gasification of coal and in some types of waste-to-energy gasification facilities. The name comes from their use as intermediates in creating synthetic natural gas (SNG) and for producing ammonia or methanol. Syngas is combustible and is often used as a fuel source or as an intermediate for the production of other chemicals.

The term "fermentor" includes a fermentation device consisting of one or more vessels and/or towers or piping arrangements, which includes the Continuous Stirred Tank Reactor (CSTR), Immobilized Cell Reactor (ICR), Trickle Bed Reactor (TBR), Moving Bed Biofilm Reactor (MBBR), Bubble Column, Gas Lift Fermenter, Membrane Reactor such as Hollow Fibre Membrane Bioreactor (HFMBR), Static Mixer, or other vessel or other device suitable for gas-liquid contact.

The terms "fermentation", "fermentation process" or "fermentation reaction" and the like are intended to encompass both the growth phase and product biosynthesis phase of the process. In one aspect, fermentation refers to conversion of CO to alcohol.

The term "cell density" means mass of microorganism cells per unit volume of fermentation broth, for example, grams/liter.

The term "increasing the efficiency", "increased efficiency" and the like, when used in relation to a fermentation process includes increasing one or more of the rate of growth of microorganisms in the fermentation, the volume or mass of desired product (such as alcohols) produced per volume or mass of substrate (such as carbon monoxide) consumed, the rate of production or level of production of the desired product, and the relative proportion of the desired product produced compared with other by-products of fermentation.

As used herein, "total alcohol" includes ethanol, butanol, propanol and methanol. In one aspect, the total alcohol may include at least about 75 weight percent or more ethanol, in another aspect, about 80 weight percent or more ethanol, in another aspect, about 85 weight percent or more ethanol, in another aspect, about 90 weight percent or more ethanol, and in another aspect, about 95 weight percent or more ethanol. In another aspect, total alcohol may include about 25 weight percent or less butanol.

The term "specific CO uptake" means an amount of CO in mmoles consumed by unit mass of microorganism cells (g) per unit time in minutes, i.e. mmole/gram/minute.

CO-Containing Substrate

A CO-containing substrate may include any gas that includes CO. In this aspect, a CO-containing gas may include syngas, industrial gases, and mixtures thereof.

Syngas may be provided from any know source. In one aspect, syngas may be sourced from gasification of carbonaceous materials. Gasification involves partial combustion of biomass in a restricted supply of oxygen. The resultant gas mainly includes CO and $H_2$. In this aspect, syngas will contain at least about 10 mole % CO, in one aspect, at least about 20 mole %, in one aspect, about 10 to about 100 mole %, in another aspect, about 20 to about 100 mole % CO, in another aspect, about 30 to about 90 mole % CO, in another aspect, about 40 to about 80 mole % CO, and in another aspect, about 50 to about 70 mole % CO. Some examples of suitable gasification methods and apparatus are provided in U.S. Ser. Nos. 61/516,667, 61/516,704 and 61/516,646, all of which were filed on Apr. 6, 2011, and in U.S. Ser. Nos. 13/427,144, 13/427,193 and 13/427,247, all of which were filed on Mar. 22, 2012, and all of which are incorporated herein by reference.

In another aspect, the process has applicability to supporting the production of alcohol from gaseous substrates such as high volume CO-containing industrial flue gases. In some aspects, a gas that includes CO is derived from carbon containing waste, for example, industrial waste gases or from the gasification of other wastes. As such, the processes represent effective processes for capturing carbon that would otherwise be exhausted into the environment. Examples of industrial flue gases include gases produced during ferrous metal products manufacturing, non-ferrous products manufacturing, petroleum refining processes, gasification of coal, gasification of biomass, electric power production, carbon black production, ammonia production, methanol production and coke manufacturing.

Depending on the composition of the CO-containing substrate, the CO-containing substrate may be provided directly to a fermentation process or may be further modified to include an appropriate $H_2$ to CO molar ratio. In one aspect, CO-containing substrate provided to the fermentor has an $H_2$ to CO molar ratio of about 0.2 or more, in another aspect, about 0.25 or more, and in another aspect, about 0.5 or more. In another aspect, CO-containing substrate provided to the fermentor may include about 40 mole percent or more CO plus $H_2$ and about 30 mole percent or less CO, in another aspect, about 50 mole percent or more CO plus $H_2$ and about 35 mole percent or less CO, and in another aspect, about 80 mole percent or more CO plus $H_2$ and about 20 mole percent or less CO.

In one aspect, the CO-containing substrate mainly includes CO and $H_2$. In this aspect, the CO-containing substrate will contain at least about 10 mole % CO, in one aspect, at least about 20 mole %, in one aspect, about 10 to about 100 mole %, in another aspect, about 20 to about 100 mole % CO, in another aspect, about 30 to about 90 mole % CO, in another aspect, about 40 to about 80 mole % CO, and in another aspect, about 50 to about 70 mole % CO. The CO-containing substrate will have a $CO/CO_2$ ratio of at least about 0.75, in another aspect, at least about 1.0, and in another aspect, at least about 1.5.

In one aspect, a gas separator is configured to substantially separate at least one portion of the gas stream, wherein the portion includes one or more components. For example, the gas separator may separate $CO_2$ from a gas stream comprising the following components: CO, $CO_2$, $H_2$, wherein the $CO_2$ may be passed to a $CO_2$ remover and the remainder of the gas stream (comprising CO and $H_2$) may be passed to a bioreactor. Any gas separator known in the art may be utilized. In this aspect, syngas provided to the fermentor will have about 10 mole % or less $CO_2$, in another aspect, about 1 mole % or less $CO_2$, and in another aspect, about 0.1 mole % or less $CO_2$.

Certain gas streams may include a high concentration of CO and low concentrations of $H_2$. In one aspect, it may be desirable to optimize the composition of the substrate stream in order to achieve higher efficiency of alcohol production and/or overall carbon capture. For example, the concentration of $H_2$ in the substrate stream may be increased before the stream is passed to the bioreactor.

According to particular aspects of the invention, streams from two or more sources can be combined and/or blended to produce a desirable and/or optimized substrate stream. For example, a stream comprising a high concentration of CO, such as the exhaust from a steel mill converter, can be combined with a stream comprising high concentrations of $H_2$, such as the off-gas from a steel mill coke oven.

Depending on the composition of the gaseous CO-containing substrate, it may also be desirable to treat it to remove any undesired impurities, such as dust particles before introducing it to the fermentation. For example, the gaseous substrate may be filtered or scrubbed using known methods.

Bioreactor Design and Operation

Descriptions of fermentor designs are described in U.S. Ser. Nos. 13/471,827 and 13/471,858, both filed May 15, 2012, and U.S. Ser. No. 13/473,167, filed May 16, 2012, all of which are incorporated herein by reference.

In accordance with one aspect, the fermentation process is started by addition of medium to the reactor vessel. Some examples of medium compositions are described in U.S. Ser. Nos. 61/650,098 and 61/650,093, filed May 22, 2012, and in U.S. Pat. No. 7,285,402, filed Jul. 23, 2001, all of which are incorporated herein by reference. The medium may be sterilized to remove undesirable microorganisms and the reactor is inoculated with the desired microorganisms. Sterilization may not always be required.

In one aspect, the microorganisms utilized include acetogenic bacteria. Examples of useful acetogenic bacteria include those of the genus *Clostridium*, such as strains of *Clostridium ljungdahlii*, including those described in WO 2000/68407, EP 117309, U.S. Pat. Nos. 5,173,429, 5,593,886 and 6,368,819, WO 1998/00558 and WO 2002/08438, strains of *Clostridium autoethanogenum* (DSM 10061 and DSM 19630 of DSMZ, Germany) including those described in WO 2007/117157 and WO 2009/151342 and *Clostridium ragsdalei* (P11, ATCC BAA-622) and *Alkalibaculum bacchi* (CP11, ATCC BAA-1772) including those described respectively in U.S. Pat. No. 7,704,723 and "Biofuels and Bioproducts from Biomass-Generated Synthesis Gas", Hasan Atiyeh, presented in Oklahoma EPSCoR Annual State Conference, Apr. 29, 2010 and *Clostridium* carboxidivorans (ATCC PTA-7827) described in U.S. Patent Application No. 2007/0276447. Other suitable microorganisms includes those of the genus *Moorella*, including *Moorella* sp. HUC22-1, and those of the genus *Carboxydothermus*. Each of these references is incorporated herein by reference. Mixed cultures of two or more microorganisms may be used.

Some examples of useful bacteria include *Acetogenium kivui, Acetoanaerobium noterae, Acetobacterium woodii, Alkalibaculum bacchi* CP11 (ATCC BAA-1772), *Blautia producta, Butyribacterium methylotrophicum, Caldanaerobacter subterraneous, Caldanaerobacter subterraneous pacificus, Carboxydothermus hydrogenoformans, Clostridium aceticum, Clostridium acetobutylicum, Clostridium acetobutylicum* P262 (DSM 19630 of DSMZ Germany), *Clostridium autoethanogenum* (DSM 19630 of DSMZ Germany), *Clostridium autoethanogenum* (DSM 10061 of DSMZ Germany), *Clostridium autoethanogenum* (DSM 23693 of DSMZ Germany), *Clostridium autoethanogenum* (DSM 24138 of DSMZ Germany), *Clostridium carboxidivorans* P7 (ATCC PTA-7827), *Clostridium coskatii* (ATCC PTA-10522), *Clostridium drakei, Clostridium ljungdahlii* PETC (ATCC 49587), *Clostridium ljungdahlii* ER12 (ATCC 55380), *Clostridium ljungdahlii* C-01 (ATCC 55988), *Clostridium ljungdahlii* O-52 (ATCC 55889), *Clostridium magnum, Clostridium pasteurianum*

(DSM 525 of DSMZ Germany), *Clostridium ragsdali* P11 (ATCC BAA-622), *Clostridium scatologenes, Clostridium thermoaceticum, Clostridium ultunense, Desulfotomaculum kuznetsovii, Eubacterium limosum, Geobacter sulfurreducens, Methanosarcina acetivorans, Methanosarcina barkeri, Morrella thermoacetica, Morrella thermoautotrophica, Oxobacter pfennigii, Peptostreptococcus productus, Ruminococcus productus, Thermoanaerobacter kivui*, and mixtures thereof The fermentation should desirably be carried out under appropriate conditions for the desired fermentation to occur (e.g. CO-to-ethanol). Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition.

The methods of the invention can be used to sustain the viability of a microbial culture, wherein the microbial culture is limited in CO, such that the rate of transfer of CO into solution is less than the uptake rate of the culture. Such situations may arise when a substrate comprising CO is not continuously provided to the microbial culture; the mass transfer rate is low; or there is insufficient CO in a substrate stream to sustain culture vitality at optimum temperature. In such embodiments, the microbial culture will rapidly deplete the CO dissolved in the liquid nutrient medium and become substrate limited as further substrate cannot be provided fast enough.

Startup: Upon inoculation, an initial feed gas supply rate is established effective for supplying the initial population of microorganisms. Effluent gas is analyzed to determine the content of the effluent gas. Results of gas analysis are used to control feed gas rates. In this aspect, the process provides a calculated CO concentration to initial cell density ratio of about 0.5 to about 0.9, in another aspect, about 0.6 to about 0.8, in another aspect, about 0.5 to about 0.7, and in another aspect, about 0.5 to about 0.6.

In another aspect, a fermentation process includes providing syngas to a fermentation medium in an amount effective for providing an initial calculated CO concentration in the fermentation medium of about 0.15 mM to about 0.70 mM, in another aspect, about 0.15 mM to about 0.50 mM, in another aspect, about 0.15 mM to about 0.35 mM, in another aspect, about 0.20 mM to about 0.30 mM, and in another aspect, about 0.23 mM to about 0.27 mM. The process is effective for increasing cell density as compared to a starting cell density.

Post-startup: Upon reaching desired levels, liquid phase and cellular material is withdrawn from the reactor and replenished with medium. The process is effective for increasing cell density to about 2.0 grams/liter or more, in another aspect, about 2 to about 30 grams/liter, in another aspect, about 2 to about 25 grams/liter, in another aspect, about 2 to about 20 grams/liter, in another aspect, about 2 to about 10 grams/liter, in another aspect, about 2 to about 8 grams/liter, in another aspect, about 3 to about 30 grams/liter, in another aspect, about 3 to about 6 grams/liter, and in another aspect, about 4 to about 5 grams/liter.

In one aspect, the process for fermenting a CO-containing substrate includes providing the CO-containing substrate to a fermentor to obtain a target CO feed rate and maintaining a CO feed rate within about seven standard deviations of the target CO feed rate. In another aspect, the process includes maintaining a CO feed rate within about six standard deviations of the target CO feed rate, in another aspect, within about five standard deviations of the target CO feed rate, in another aspect, within about four standard deviations of the target CO feed rate, in another aspect, within about three standard deviations of the target CO feed rate, in another aspect, within about two standard deviations of the target CO feed rate, and in another aspect, within about one standard deviations of the target CO feed rate.

In one aspect, the process includes cycling the CO feed rate between a target CO feed rate and about seven standard deviations from the target CO feed rate. In another aspect, the CO feed rate is within about four to about seven standard deviations of the target CO feed rate for at least about 1% to about 20% of a total fermentation time after achieving the target CO feed rate. In another aspect, the CO feed rate is within about 4.5 to about 6.5 standard deviations of the target CO feed rate for at least about 3% to about 15% of a total fermentation time after achieving the target CO feed rate. In another aspect, the CO feed rate is within about six to about 6.5 standard deviations of the target CO feed rate for at least about 5% to about 12% of a total fermentation time after achieving the target CO feed rate, and in another aspect, about 6% to about 12% of a total fermentation time after achieving the target CO feed rate.

In another aspect, the process includes cycling the CO feed rate between a target CO feed rate and within about three to about five standard deviations of the target CO feed rate for at least about 1% to about 10% of a total fermentation time after achieving the target CO feed rate. In another aspect, the CO feed rate is within about three to about four standard deviations of the target CO feed rate for at least about 1% to about 10% of a total fermentation time after achieving the target CO feed rate, in another aspect, about 1% to about 7% of a total fermentation time after achieving the target CO feed rate, and in another aspect, about 1% to about 5% of a total fermentation time after achieving the target CO feed rate.

In another aspect, the process includes cycling the CO feed rate between a target CO feed rate and within about one to about three standard deviations of the target CO feed rate for at least about 1% to about 10% of a total fermentation time after achieving the target CO feed rate. In another aspect, the CO feed rate is within about two to about three standard deviations of the target CO feed rate for at least about 1% to about 10% of a total fermentation time after achieving the target CO feed rate, in another aspect, about 1% to about 6% of a total fermentation time after achieving the target CO feed rate, and in another aspect, about 1% to about 5% of a total fermentation time after achieving the target CO feed rate.

In a related aspect, once a target feed rate is achieved, actual CO feed rates are monitored. An average CO feed rate is determined by measuring CO feed rates at least 3 times while the CO feed rate is within a target CO feed rate range. Measurements of CO feed rates may be made 3 or more times, in another aspect, any number of times, such as for example any number of measurements from about 4 to about 50. A standard deviation may then be calculated based on an average CO feed rate.

In one aspect, the process includes cycles of decreasing and increasing CO feed rates in any manner effective for providing desired CO concentrations, $H_2$ conversions, or CO uptake. In one aspect, the process includes reducing the target CO feed rate by about 35% or less for about 20 minutes or less. In another aspect, the process includes reducing the target CO feed rate to the fermentation by about 25% to about 35%, in another aspect, about 26% to about 34%, and in another aspect, about 28% to about 32%, to provide a first reduced CO feed rate. The first reduced CO feed rate is maintained for about 1 to about 10 minutes, in another aspect, about 2 to about 8 minutes, in another aspect, about 3 to about 7 minutes, and in another aspect, about 4 to about 6 minutes.

In accordance with another aspect of the process, the process includes increasing the first reduced CO feed rate to provide a second reduced CO feed rate that is reduced by about 15% to about 25%, in another aspect, about 17% to about 23%, and in another aspect, about 18% to about 22%, of the target CO feed rate. The process further includes maintaining the second reduced CO feed rate for about 1 to about 5 minutes, in another aspect, about 1 to about 4 minutes, and in another aspect, about 1 to about 3 minutes.

In accordance with another aspect of the process, the process includes increasing the second reduced CO feed rate to provide a third reduced CO feed rate that is reduced by about 5% to about 15%, in another aspect, about 7% to about 13%, and in another aspect, about 8% to about 12%, of the target CO feed rate. The process further includes maintaining the third reduced CO feed rate for about 1 to about 5 minutes, in another aspect, about 1 to about 4 minutes, and in another aspect, about 1 to about 3 minutes. The process may further include increasing the third reduced CO feed rate to the target feed rate or to more than the target feed rate. Cycles of increasing and decreasing CO feed rates may be repeated at least about once per hour, and in another aspect, and any number of times ranging form 1 to 20 cycles per hour. Cycles of increasing and decreasing CO feed rates may be continued until the end of the fermentation.

Figure 1B:
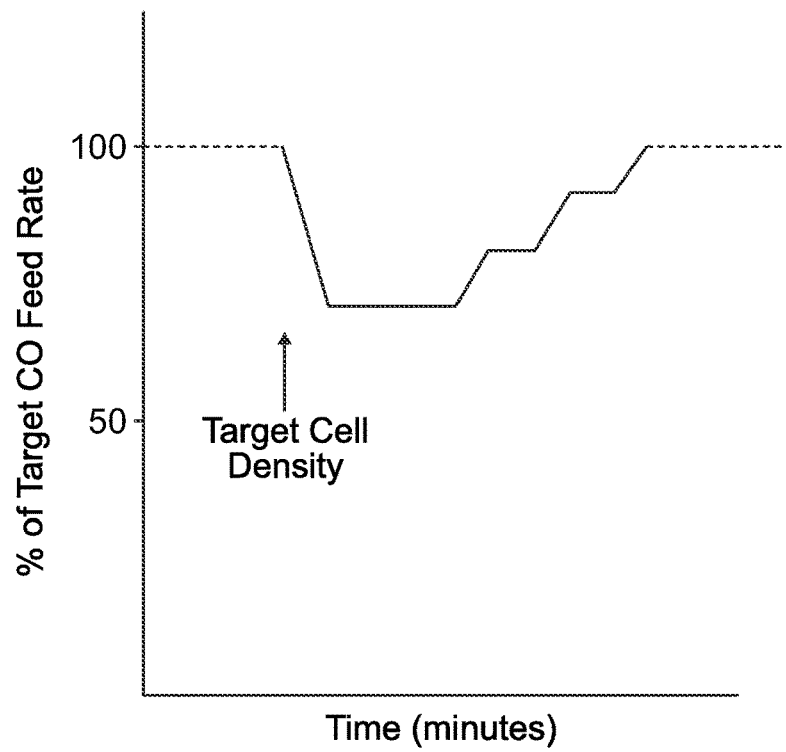

FIGS. 1(a) and 1(b) show two examples of variations of repetitive patterns of cycling CO to a fermentation. In the two graphs shown in FIGS. 1(a) and 1(b), the x-axis is time and the y-axis is the % reduction of target CO feed rate. FIG. 1(a) illustrates a straight step pattern where flow rates are quickly adjusted. FIG. 1(b) shows a gradual step pattern where flow rates are more gradually adjusted. The repetitive patterns are not limited to those shown in FIGS. 1(a) and 1(b), but may include any type of pattern that allows for cycling CO flow rates.

CO feed rates may be expressed in standard cubic feet per minute (SCFM) or in standard cubic feet per hour per liter. In this aspect, the standard cubic feet per hour per liter may be in a range of about 0.9 to about 2.0, and in another aspect, about 1.25 to about 1.75 SCFM. In another aspect, the average CO feed rate is a CO feed rate effective for maintaining a ratio of CO feed rate to the fermentor to fermentor volume of about 0.016:1 to about 0.04:1, in another aspect, about 0.02:1 to about 0.04:1, in another aspect, about 0.02:1 to about 0.035:1, in another aspect, about 0.025:1 to about 0.035:1, and in another aspect, about 0.025:1 to about 0.03:1.

In another aspect, the process includes monitoring the $H_2$ conversion and maintaining an $H_2$ conversion of about 25% or more, in another aspect, about 25% to about 95%, in another aspect, about 30% to about 90%, in another aspect, about 35% to about 85%, in another aspect, about 40% to about 80%, in another aspect, about 40% to about 70%, in another aspect, about 40% to about 60%, and in another aspect, about 40% to about 50%. The process may further include monitoring CO uptake and maintaining a CO uptake of about 0.001 to about 10 mmole/minute/gram of dry cells, in another aspect, about 0.001 to about 5 mmole/minute/gram of dry cells, in another aspect, about 0.001 to about 4 mmole/minute/gram of dry cells, in another aspect, about 0.001 to about 3 mmole/minute/gram of dry cells, in another aspect, about 0.001 to about 2 mmole/minute/gram of dry cells, in another aspect, about 0.001 to about 1 mmole/minute/gram of dry cells, in another aspect, about 0.05 to about 9 mmole/minute/gram of dry cells, in another aspect, about 0.05 to about 5 mmole/minute/gram of dry cells, in another aspect, about 0.05 to about 4 mmole/minute/gram of dry cells, in another aspect, about 0.05 to about 3 mmole/minute/gram of dry cells, in another aspect, about 0.05 to about 2 mmole/minute/gram of dry cells, in another aspect, about 0.05 to about 1 mmole/minute/gram of dry cells, in another aspect, about 1 to about 8 mmole/minute/gram of dry cells, in another aspect, about 1 to about 5 mmole/minute/gram of dry cells, in another aspect, about 1 to about 4 mmole/minute/gram of dry cells, in another aspect, about 1 to about 3 mmole/minute/gram of dry cells, and in another aspect, about 1 to about 2 mmole/minute/gram of dry cells.

In another aspect, the process is effective for maintaining a calculated CO concentration (mM) to cell density (grams/liter) ratio of about 0.001 to about 1.0. In another aspect, a calculated CO concentration to cell density ratio of about 0.01 to about 0.9, in another aspect, about 0.01 to about 0.8, in another aspect, about 0.02 to about 0.8, in another aspect, about 0.02 to about 0.75, in another aspect, about 0.03 to about 0.75, and in another aspect, about 0.03 to about 0.5.

Determination of CO Concentrations—Calculated Value

Dissolved CO concentration was calculated per the following formula.

$$P_{co}^L = \frac{CO_{in} - CO_{out}}{\ln(CO_{in}/CO_{out})} * (P_{101} + 14.7) - \frac{q_{co}}{V \cdot K_L \alpha} \times 1200 \times 14.7$$

Upon gas reduction, dissolved CO will be reduced as well due to reduced CO partial pressure in the off gas and reduced $K_L a$ (mass transfer coefficient). When there was no gas cycling, the dissolved CO remained relatively stable.

The process is effective for maintaining a dissolved CO concentration of about 0.25 mM or less, in another aspect, about 0.20 mM or less, in another aspect, about 0.15 mM or less, in another aspect, about 0.10 mM or less, in another aspect, about 0.08 mM or less, and in another aspect about 0.06 mM or less. In another aspect, the dissolved CO concentration may be as low as a limit of detection of CO and may be essentially zero.

EXAMPLES

Example 1

Gas Cycling

A fermentation was conducted with *Clostridium ljungdahlii*. After initial startup, the fermentation experienced performance upset signaled by declining $H_2$ conversion. Gas cycle was implemented at hour 126 when $H_2$ conversion was at 23.5%.

Gas cycling was conducted as follows: Reduce gas flow rate by 30% for 5 minutes→Ramp back from −30% to −20% for a further 2 minutes→Ramp back from −20% to −10% for a further 2 minutes→Ramp back to original flow rate; repeat this process every 1 hour.

Figure 2:
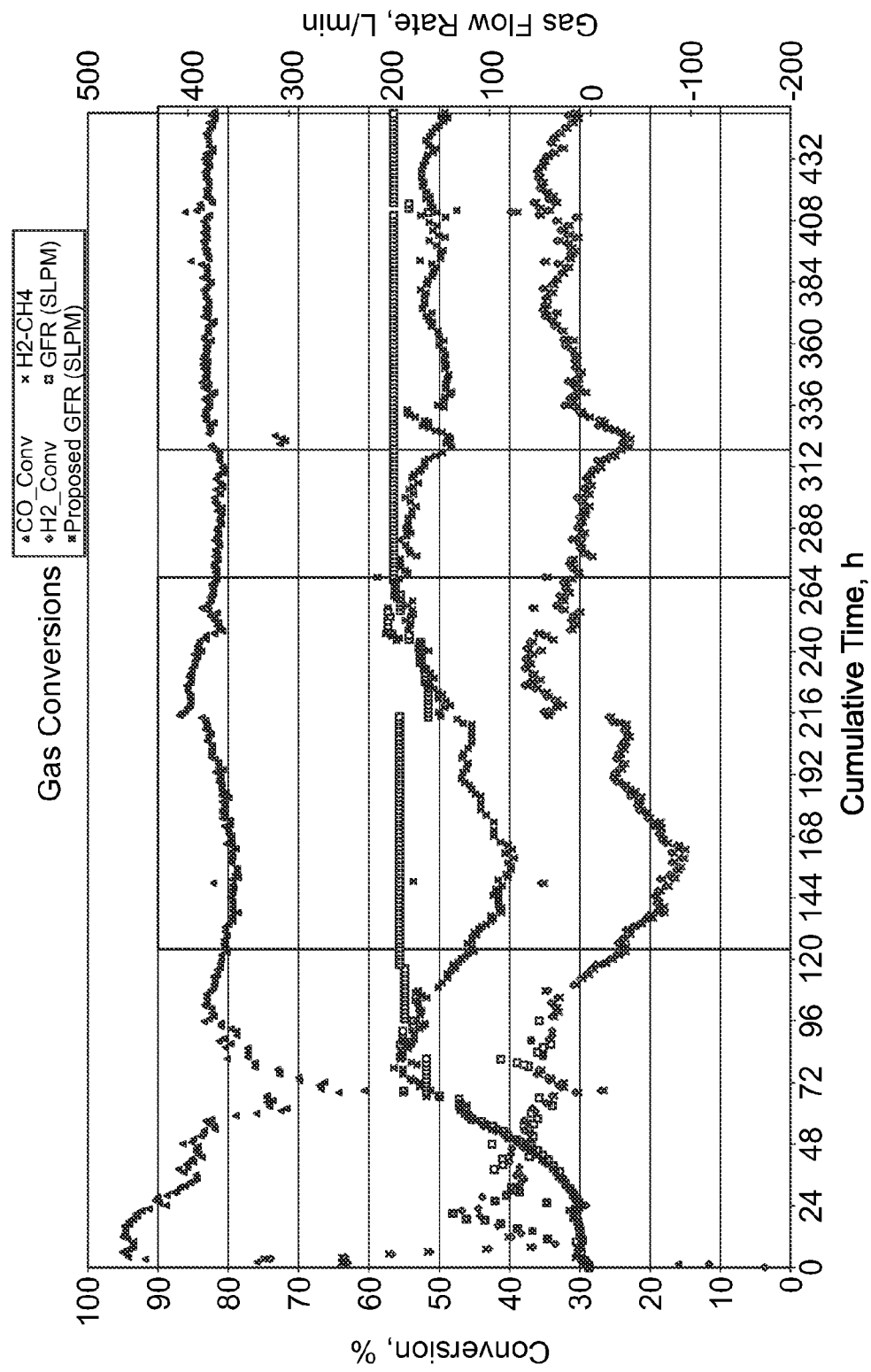
FIG. 2 illustrates results from a fermentation with varying gas flow rates.

Fermentation results are illustrated in FIG. 2. $H_2$ uptake continued to decline during gas cycle treatment, and $H_2$ conversion bottomed at 160 hour at 15.6%. $H_2$ conversion reversed trend and increased and peaked at hour 237 and maintained for the next 30 hours. Gas cycle was intentionally stopped at hour 270 to: a) to potentially reduce risk of high acid; and b) to verify that $H_2$ conversion will decline, and make a gas cycle re-test possible. Both ethanol and acid started coming down after a day (at hour 296) with hydrogen conversion trending down. $H_2$ conversion drop accelerated during the time period of 308 to 316. Gas cycle was resumed when $H_2$ conversion hit 24% at 319 hour. Dissolved CO during gas cycling was in a range of 3.1 to 3.8 psia.

Improved hydrogen conversion was seen 6 hours later after the gas-cycle was resumed and hydrogen conversion was improved to 32% in 20 hours. Gas cycle was kept on through the rest of fermentation.

Example 2

Recovery of $H_2$ Conversion Using Gas Cycling

Figure 3:
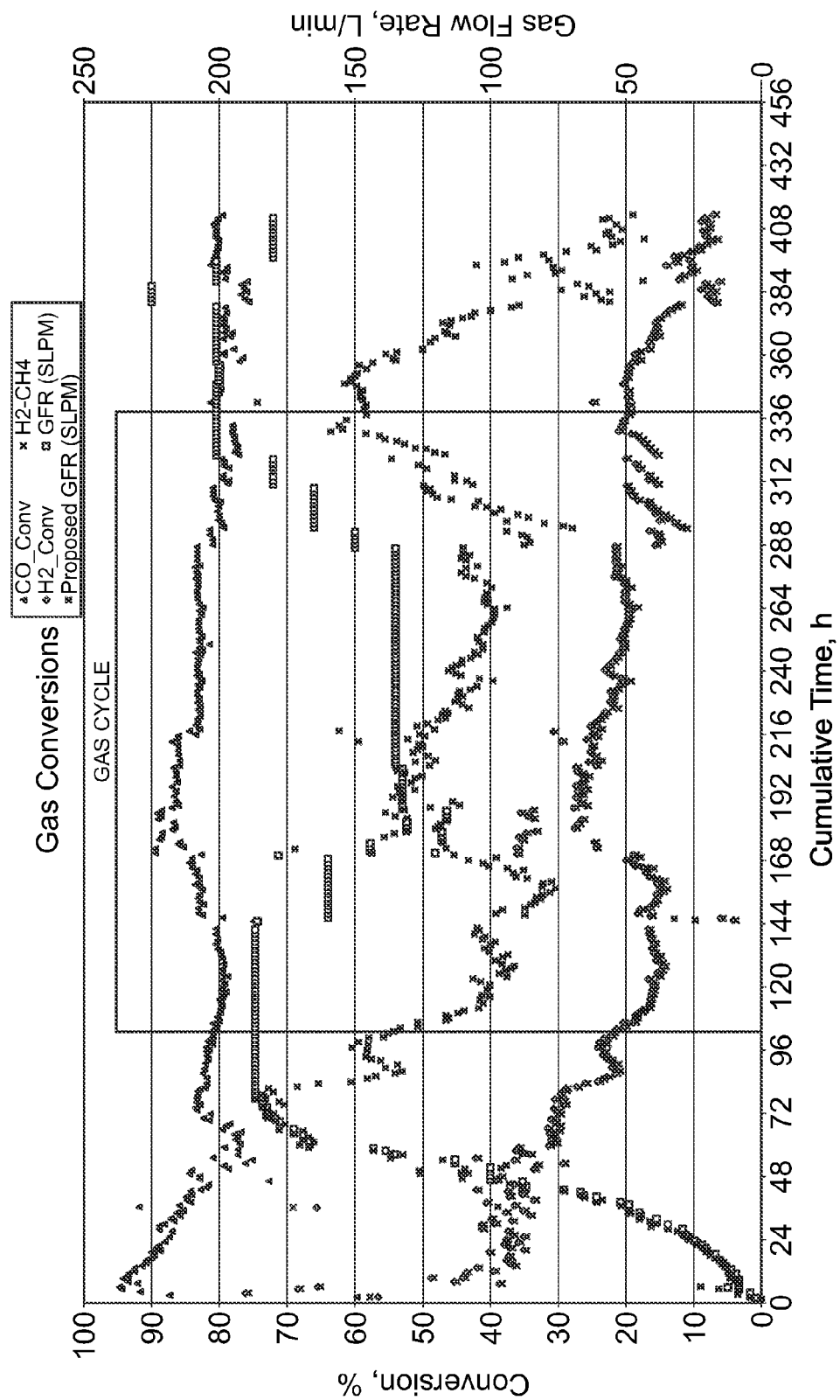
FIG. 3 shows the effect of gas cycling on $H_2$ conversion.

A fermentation was conducted with *Clostridium ljungdahlii*. As illustrated in FIG. 3, fermentation had low hydrogen conversion throughout the run. Gas cycling was implemented during the down trend of hydrogen conversion, and was able to restore the conversation. When gas cycling was removed from the process, the hydrogen conversion declined. Dissolved CO during gas cycling was in a range of 3.1 to 4.1 psia.

Example 3

Recovery of $H_2$ Conversion Using Gas Cycling

Figure 4:
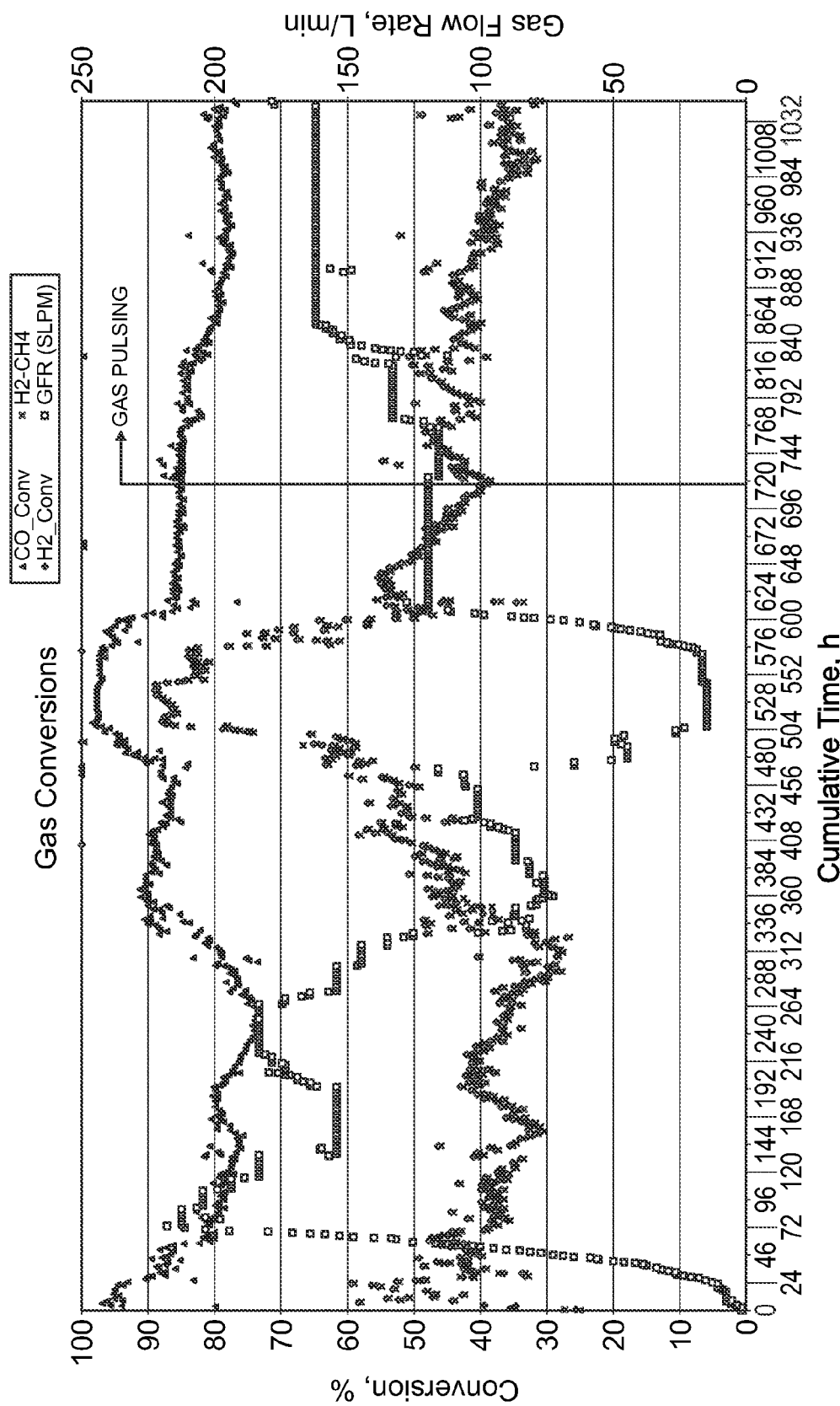
FIG. 4 illustrates restoration of $H_2$ conversion after resuming gas flow cycling.

A fermentation was conducted with *Clostridium ljungdahlii*. As shown in FIG. 4, prior to 480 hours, gas cycle was implemented as described, then was off from 480-600 hours when the fermentor ran at low cell density. At 624 hours, the fermentor was re-ramped up, however, gas cycle was left off until 722 hours process time. The hydrogen conversion had been declining from 50% (and above) down to 40% under constant gas flow rate. $H_2$ conversion was recovered back to upper 40 s after gas cycling was reinstated. Dissolved CO during gas cycling was in a range of 2.2-3.2 psia.

Example 4

Gas Cycling with Pilot Plant Fermentor

A pilot plant main fermentor was operated according to the following conditions prior to starting any gas cycling.
  Reactor Volume: 245 liters
  Gas feed rate: 6 SCFM
  Gas composition: 15% $H_2$, 10% $CO_2$, 30% CO, and 45% $N_2$
  Agitation was maintained at 38 Hz or 355 rpm.
  Fermentor operation pressure was 45 psig with 50% full of liquid with temperature controlled jacket.
  The theoretical ethanol productivity (assume all converted gas is to produce ethanol) was about 125 g/L day with water recycle system turn on.
  CO and $H_2$ conversions were around 77% and 42%.
  Ethanol and acetyl concentration were 23 and 2.3 g/L.
  Cell retention time was 19 hour and liquid retention time was 4.4 hr.
  Gas cycling was as follows: The gas flow rate was increased 10% in the first 10 minutes every hour and then returned back to the starting gas feed rate for 50 minutes. In the next hour, the gas flow rate was reduced 10% for 10 minutes then back to the starting gas feed rate again for 50 minutes.

The fermentor was operated under the starting gas feed rate of 6 SCFM for about one day. The gas rate was reduced to 5.4 SCFM by reducing the gas feed rate 0.1 SCFM every 2 hours. Then the gas feed rate was maintained at 5.4 SCFM for another 54 hours. Gas cycling was changed to a 20% increase and decrease for a duration 15 minutes. The fermentor operated under 20% cycling for another 76 hours without any difficulty. The cycling magnitude was then increased to 50% with duration extended to 4 hours and cycle times to 8 hours.

Figure 5:
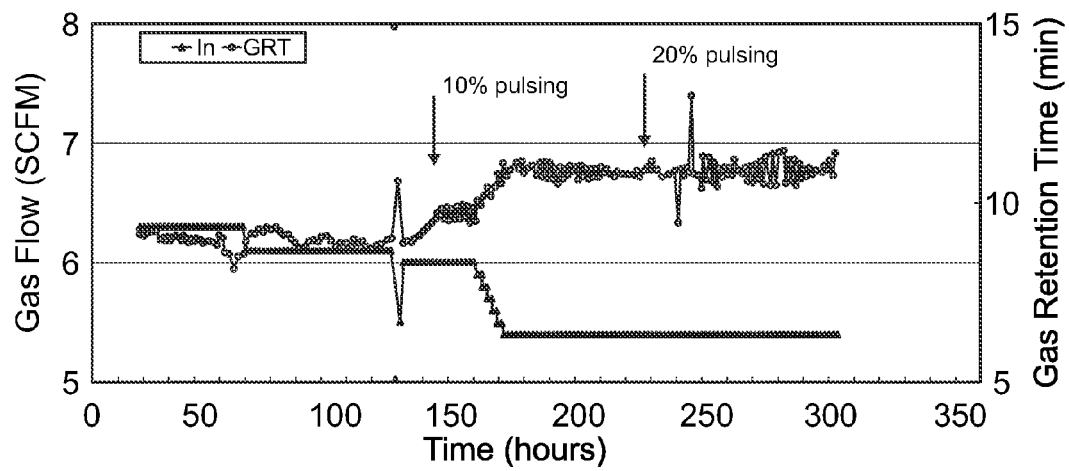
FIG. 5 shows gas retention times and flow rates in a pilot plant fermentor.

The performance of 10% and 20% magnitude cycling are shown in FIGS. 5 to 10. FIG. 5 shows the gas feed rate and gas retention time in the run. The gas feed rate is based on the base gas feed rate and the gas retention time is based on the gas feed rate recorded during hourly sampling. The measured data is once per hour. As shown in FIG. 5, the gas retention time after cycling stable on a flat line with some oscillation with constant magnitude and frequency when measured during the cycling period. Oscillation magnitude was higher during 20% gas cycling than 10% gas cycling when measured during cycling.

Figure 6:
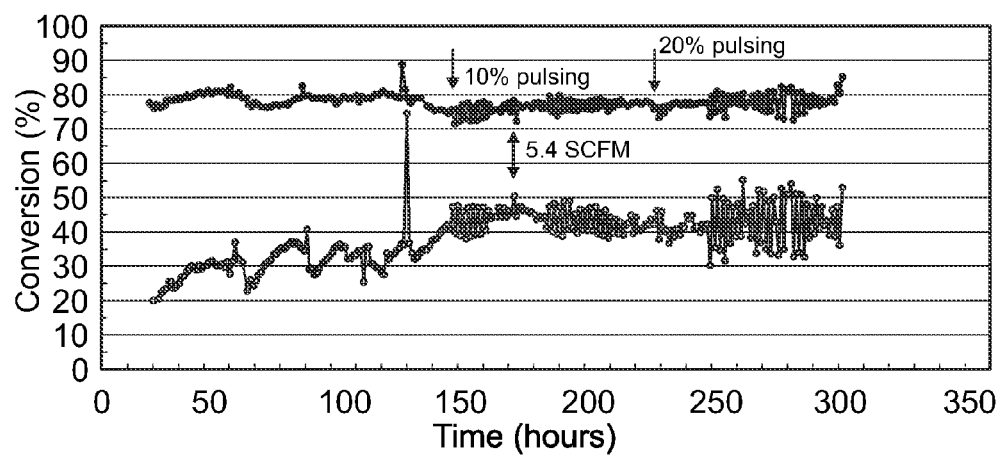
FIG. 6 shows gas conversions in a pilot plant fermentor with 10% and 20% gas flow rate variations.

FIG. 6 shows $H_2$ and CO conversion. The figure includes five days of sampling before cycling. CO conversion was more irregular before cycling as compared to after cycling. $H_2$ conversion before cycling was significantly more unstable and the magnitude of zigzag was wider and frequency was irregular. After gas cycling, the $H_2$ conversion was stable around 44% with regular oscillation.

Figure 7:
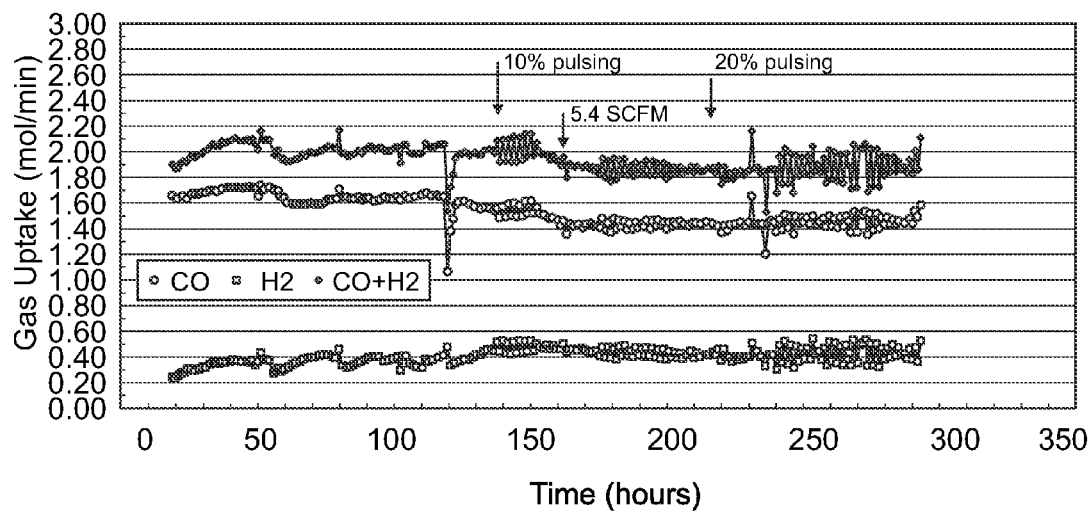
FIG. 7 illustrates substrate uptake in a pilot plant fermentor.

FIG. 7 is similar to the conversion as shown in FIG. 5 except it also includes the effect from gas feed rate. CO uptake before cycling was higher than after cycling due to higher gas feed rates. $H_2$ uptake was higher after cycling.

Figure 8:
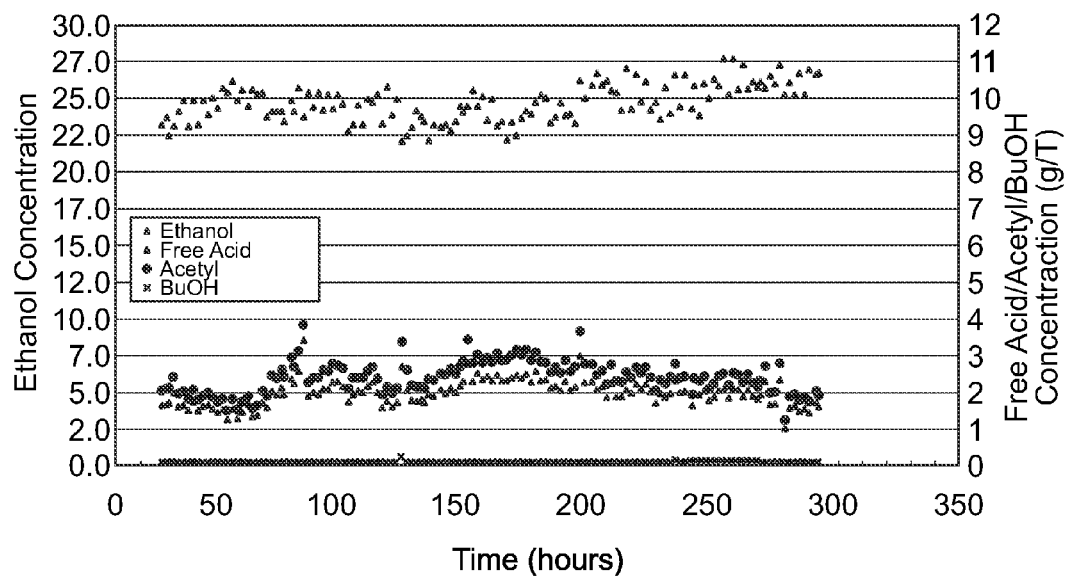
FIG. 8 illustrates product concentrations in a pilot plant fermentor.

FIG. 8 shows product concentration before and after cycling. In general ethanol concentration increased and acetic acid concentration decreased after cycling.

Figure 9:
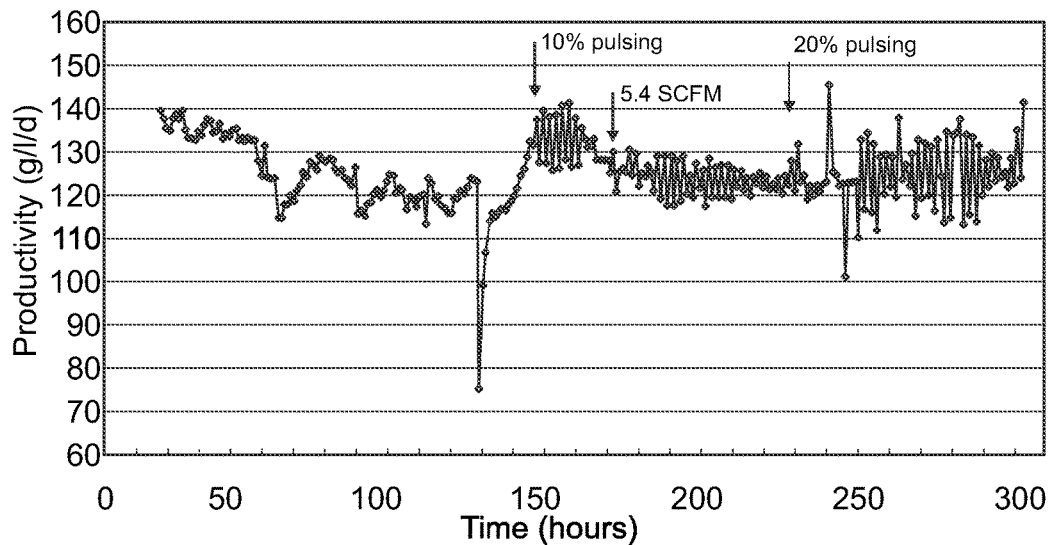
FIG. 9 illustrates the effect of gas cycling rates on theoretical ethanol productivity in a pilot plant fermentor.

FIG. 9 shows the theoretical productivity before and after gas cycling. Theoretical productivity assumes all the syngas consumed goes to ethanol production.

Figure 10:
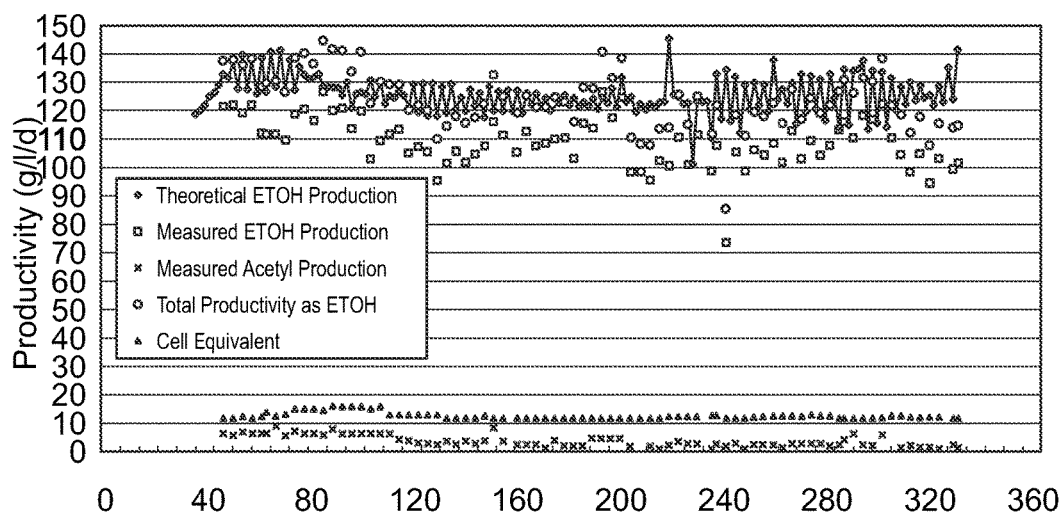
FIG. 10 shows ethanol productivity in the pilot plant fermentor.

FIG. 10 shows the actual productivity which is based on measured liquid product concentration and liquid flow rate, not from gas uptake calculations.

Another method to realize the advantage of gas cycling is based on average of the same operation zone. Table 1 lists the average CO and $H_2$ conversion and uptake as well as theoretical productivity for gas cycling vs. no gas cycling. Table 2 lists the average product concentrations and cell concentration during the same period. The 10% cycling of syngas feed rate around 6 SCFM increased $H_2$ conversion from 39-42% range to 44.5%, but only slightly affected CO conversion. This might slightly enhance the theoretical productivity. There was a trend of increasing $H_2$ conversion and reducing of CO conversion after the upset. If only counting the last few hours before gas cycling, $H_2$ conversion was around 42.8%, still lower than the average of 44.5% after cycling. CO conversion was very close, 76.45% vs. 76.33%. If based on the two 13 hours of no cycling, 6 SCFM runs, average $H_2$ conversion was 38.92% and CO conversion was 77.98%. The 10% cycling decreased 1.65% CO conversion but increased about 5.56% $H_2$ conversion. The theoretical productivity slightly increased from 128.06 to 133.12 g/L day. Average ethanol and acetic acid concentration without cycling was 23.65 and 2.23 g/L. The cycling increased ethanol concentration to 24.31 g/L and acetic acid concentration to 2.83 g/L.

The advantage was more obviously in cycling around 5.4 SCFM. Not only average $H_2$ conversion was higher, 44-45% vs. 33-42%, but also theoretical productivity was higher, 124-125 g/L day vs. 112.5-114 g/L day.

The change in cycling magnitude from 10 to 20% only slightly affects the average conversion and productivity. CO conversion increased about 0.85% and $H_2$ conversion reduced about 0.75%. Average ethanol concentration slightly increased from 24.72 to 25.92 g/L, acetic acid concentration reduced from 2.73 to 2.23 g/L.

TABLE 1

Average gas conversions, uptake and theoretical productivity.

| Duration, hr | Base Gas, SCFM | Cycling % | CO Conv., % | $H_2$ Conv.,% | Theo. STY, g/L day | CO uptake, mmole/min | $H_2$ uptake, mmole/min |
|---|---|---|---|---|---|---|---|
| 17 | 5.4 | 0 | 77.55 | 41.81 | 114.09 | 1.406 | 0.404 |
| 31.5 | 5.4 | 0 | 78.68 | 32.65 | 112.49 | 1.404 | 0.318 |
| 13 | 6.0 | 0 | 78.25 | 39.37 | 134.98 | 1.607 | 0.433 |
| 42 | 6.3 | 0 | 79.34 | 28.72 | 131.79 | 1.690 | 0.330 |
| 58 | 6.1 | 0 | 78.85 | 34.31 | 121.77 | 1.633 | 0.375 |
| 1* | 3.5->5 | 0 | 89.28 | 76.07 | 75.28 | 1.065 | 0.477 |
| 2* | 5.0->6.0 | 0 | 79.64 | 35.46 | 106.58 | 1.432 | 0.340 |
| 13 | 6.0 | 0 | 77.71 | 38.46 | 121.13 | 1.578 | 0.412 |
| 6# | 6.0 | 0 | 76.76 | 41.85 | 127.61 | 1.558 | 0.447 |
| 3# | 6.0 | 0 | 76.45 | 42.81 | 131.00 | 1.552 | 0.456 |
| 1# | 6.0 | 0 | 76.34 | 42.16 | 131.61 | 1.547 | 0.448 |
| 14 | 6.0 | 10% | 76.33 | 44.48 | 133.12 | 1.549 | 0.480 |
| 10 | 6.0->5.4 | 10% | 77.74 | 47.13 | 130.24 | 1.493 | 0.475 |
| 54 | 5.4 | 10% | 78.57 | 44.88 | 123.88 | 1.433 | 0.434 |
| 76 | 5.4 | 20% | 79.43 | 44.12 | 124.98 | 1.451 | 0.425 |

*Up-set in transferring gas. Gas feed rate was down to 3.5 SCFM and than increased back to 5.0 SCFM within one hour. Gas flow rate increased slowly to 6.0 SCFM within next two hours.
only using the last few hours data before gas cycling.

TABLE 2

Average products and cell concentration

| Duration, hr | Base Gas, SCFM | Cycling % | Cell Conc., g/L | ETOH Conc., g/L | HAc Conc., g/L | BTOH Conc., g/L |
|---|---|---|---|---|---|---|
| 17 | 5.4 | 0 | 9.626 | 26.70 | 1.39 | 0.34 |
| 31.5 | 5.4 | 0 | 7.243 | 21.04 | 2.60 | 0.68 |
| 13 | 6.0 | 0 | 8.832 | 23.95 | 2.20 | 0.13 |
| 42 | 6.3 | 0 | 9.044 | 24.605 | 1.879 | 0.050 |
| 58 | 6.1 | 0 | 9.064 | 24.560 | 2.460 | 0.041 |
| 1* | 3.5->5 | 0 | 8.413 | 22.17 | 3.35 | 0.18 |
| 2* | 5.0->6.0 | 0 | 8.446 | 22.365 | 2.975 | 0.1 |
| 13 | 6.0 | 0 | 9.35 | 23.355 | 2.255 | 0.028 |
| 6# | 6.0 | 0 | 9.663 | 23.225 | 2.405 | 0.025 |
| 3# | 6.0 | 0 | 9.728 | 23.16 | 2.50 | 0.02 |
| 14 | 6.0 | 10% | 10.329 | 24.307 | 2.830 | 0.031 |
| 10 | 6.0->5.4 | 10% | 10.306 | 24.144 | 2.878 | 0.030 |
| 54 | 5.4 | 10% | 8.80 | 24.724 | 2.729 | 0.040 |
| 76 | 5.4 | 20% | 8.934 | 25.924 | 2.228 | 0.042 |

*Up-set in transferring gas. Gas feed rate was down to 3.5 SCFM and than increased back to 5.0 SCFM within one hour. Gas flow rate increased slowly to 6.0 SCFM within next two hours.
only using the last few hours data before gas cycling.

While the invention herein disclosed has been described by means of specific embodiments, examples and applications thereof, numerous modifications and variations could be made thereto by those skilled in the art without departing from the scope of the invention set forth in the claims.

What is claimed is:

1. A process for fermenting a CO-containing substrate, the process comprising:
    providing the CO-containing substrate to a fermentor; and
    fermenting the CO-containing substrate with an acetogenic bacteria,
    wherein a CO feed rate is cycled within four to seven standard deviations of a target CO feed rate for at least 1% to 20% of a total fermentation time after achieving the target CO feed rate, wherein the target CO feed rate is 4 to 8 standard cubic feet per minute (SCFM), and cycles include increasing and decreasing the CO feed rate at least once per hour,
    wherein the CO feed rate maintains a dissolved CO concentration in the fermentation medium of 0.25 mM or less, and the fermentation process provides an STY of 10 g total alcohol/ (L·day) or more.

2. The process of claim 1 wherein the target CO feed rate is effective for providing a target cell density.

3. The process of claim 2 wherein the target cell density is 3 g/L to 30 g/L.

4. The process of claim 1 wherein the CO-containing substrate provided to the fermentor has a $CO/CO_2$ molar ratio of 0.75 or more.

5. The process of claim 1 wherein the acetogenic bacteria is selected from the group consisting of *Acetogenium kivui, Acetoanaerobium noterae, Acetobacterium woodii, Alkalibaculum bacchi* CP11 ATCC BAA-1772, *Blautia producta, Butyribacterium methylotrophicum, Caldanaerobacter subterraneous, Caldanaerobacter subterraneous pacificus, Carboxydothermus hydrogenoformans, Clostridium aceticum, Clostridium acetobutylicum, Clostridium autoethanogenum* DSM 19630 of DSMZ Germany, *Clostridium autoethanogenum* DSM 10061 of DSMZ Germany, *Clostridium autoethanogenum* DSM 23693 of DSMZ Germany, *Clostridium autoethanogenum* DSM 24138 of DSMZ Germany, *Clostridium carboxidivorans* P7 ATCC PTA-7827, *Clostridium coskatii* ATCC PTA-10522, *Clostridium drakei, Clostridium ljungdahlii* PETC ATCC 49587, *Clostridium ljungdahlii* ERI2 ATCC 55380, *Clostridium ljungdahlii* C-01 ATCC 55988, *Clostridium ljungdahlii* O-52 ATCC 55889, *Clostridium magnum, Clostridium pasteurianum* DSM 525 of DSMZ German, *Clostridium ragsdali* P11 ATCC BAA-622, *Clostridium scatologenes, Clostridium thermoaceticum, Clostridium ultunense, Desulfotomaculum kuznetsovii, Eubacterium limosum, Geobacter sulfurreducens, Methanosarcina acetivorans, Methanosarcina barkeri, Morrella thermoacetica, Morrella thermoautotrophica, Oxobacter pfennigii, Peptostreptococcus productus, Ruminococcus productus, Thermoanaerobacter kivui,* and mixtures thereof.

* * * * *